US008374687B2

(12) United States Patent
Mathan et al.

(10) Patent No.: US 8,374,687 B2
(45) Date of Patent: Feb. 12, 2013

(54) RAPID SERIAL VISUAL PRESENTATION TRIAGE PRIORITIZATION BASED ON USER STATE ASSESSMENT

(75) Inventors: Santosh Mathan, Minneapolis, MN (US); Michael C. Dorneich, St. Paul, MN (US); Patricia M. Ververs, Ellicott City, MD (US); Stephen D. Whitlow, St. Louis Park, MN (US)

(73) Assignee: Honeywell International Inc., Morristown, NJ (US)

( * ) Notice: Subject to any disclaimer, the term of this patent is extended or adjusted under 35 U.S.C. 154(b) by 2155 days.

(21) Appl. No.: 11/336,516

(22) Filed: Jan. 21, 2006

(65) Prior Publication Data

US 2007/0236488 A1    Oct. 11, 2007

(51) Int. Cl.
*A61B 5/0476* (2006.01)
*A61B 5/05* (2006.01)
(52) U.S. Cl. ......................... 600/544; 600/407
(58) Field of Classification Search .................. None
See application file for complete search history.

(56) References Cited

U.S. PATENT DOCUMENTS

| 6,092,058 | A  | * | 7/2000 | Smyth .............................. 706/10 |
| 2005/0159671 | A1 | * | 7/2005 | Sneddon ....................... 600/544 |
| 2007/0049844 | A1 | * | 3/2007 | Rosenfeld ..................... 600/544 |

OTHER PUBLICATIONS

Dorneich et al., "A Joint Human-Automation Congnitive System to Support Rapid Decision-Making in Hostile Environments", "Systems, Man and Cybernetics, 2005 IEEE International Conference", Oct. 2005, pp. 2390-2395, Publisher: IEEE.
Erdogmus et al., "Cognitive State Estimation Based on EEG for Augmented Cognition", "Proceedings of the 2nd International IEEEE EMBS Conference on Neural Engineering ", Mar. 2005, pp. 566-569, Publisher: IEEE.
Mathan et al., "Sensor-Based Cognitive State Assessment in a Mobile Enviroment " "Proceedings of the 11th Conference on Human Computer Interaction", Jul. 2005, pp. 1-10.
Parra et al., "Response Error Correction—A Demonstration of Improved Human-Machine Performance Using Real-Time EEG Monitoring", "IEEE Transactions on Neural Systems and Rehabilitation Engineering", Jun. 2003, pp. 173-177, vol. 11, No. 2, Publisher: IEEE.
Parra et al., "Recipes for the Linear Analysis of EEG", "Neuroimage", Nov. 2005, pp. 326-341, vol. 28, No. 2, Publisher: Academic Press, Published in: Orlando, FL.

(Continued)

*Primary Examiner* — Long V. Le
*Assistant Examiner* — Lawrence Laryea
(74) *Attorney, Agent, or Firm* — Ingrassia Fisher & Lorenz, P.C.

(57) ABSTRACT

A method and system are provided that prioritize the output of an image triage that is based on rapid serial visual presentation. User responses and estimates of the effectiveness with which each image is likely to have been processed by a user are employed for post triage image prioritization of potential targets. Images associated with a user response, processed during optimal user states, are assigned the highest priority for post triage examination, as targets are likely. Images without a user response that are processed during optimal user states are assigned the lowest priority, as these are unlikely to contain targets. Images with a user response that are processed during suboptimal states are assigned a medium priority, as these are likely to contain a high number of false positives. Images without a user response, processed during suboptimal user states are flagged for reprocessing as these may contain targets that the user may not have detected.

18 Claims, 3 Drawing Sheets

OTHER PUBLICATIONS

Ruta et al., "An Overview of Classifier Fusion Methods", "Computing and Information Systems", Feb. 2000, pp. 1-10, vol. 7, No. 1, Publisher: Univeristy of Paisley, Published in: United Kingdom.

Sajda et al., "High0throughput Image Search Via Single-Trial Event Detection in a Rapid Serial Visual Presentation Task", "First International IEEE EMBS Conference on Neural Engineering", 2003, pp. 7-10, Publisher: IEEE.

Sajda et al., "Spatial Signatures of Visual Object Recognition Events Learned From Single-Trial Analysis of EEG", "Proceedings of the 25th Annual International Confrence of the IEEE Engineering in Medicine and Biology Society", 2003, pp. 2087-2090, vol. 3, Publisher: IEEE, Published in: Piscataway, NJ.

Thorpe et al., "Speed of Processing in the Human Visual System", "Nature ", Jun. 1996, pp. 520-522, vol. 381, No. 6582, Publisher: Macmillan Magazines UK, Published in: United Kingdom.

* cited by examiner

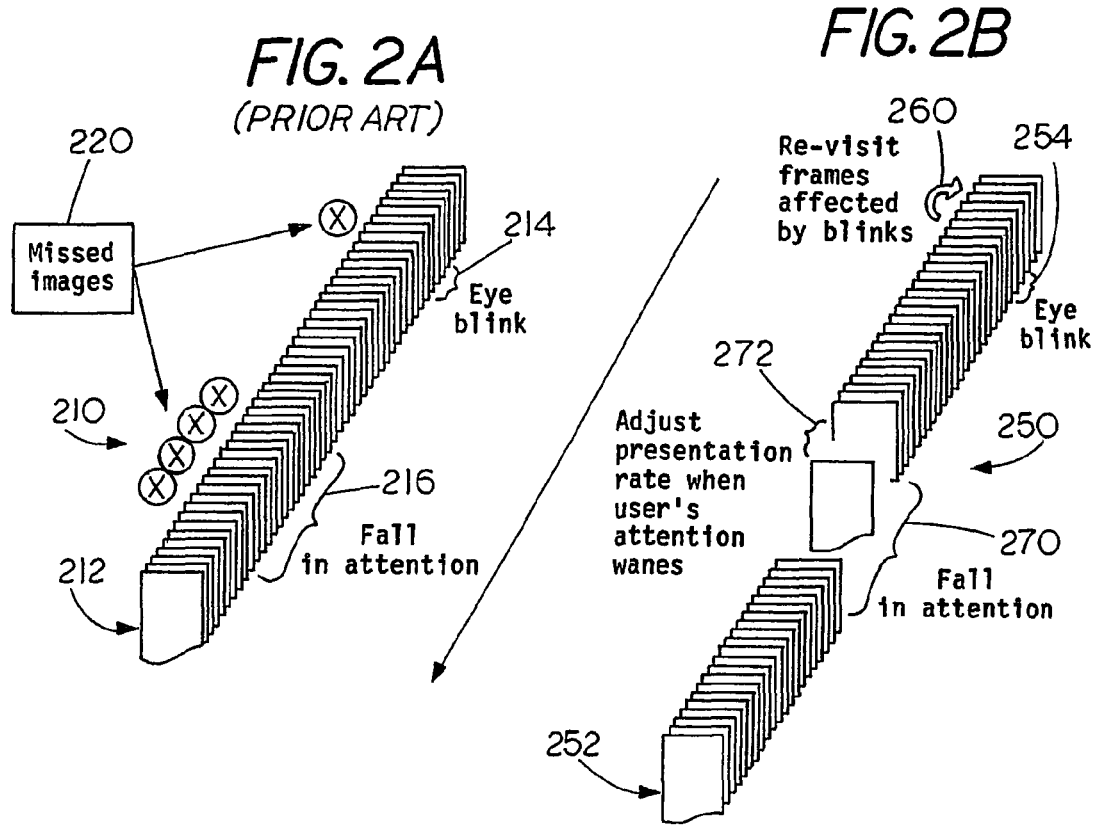

RAPID SERIAL VISUAL PRESENTATION TRIAGE PRIORITIZATION BASED ON USER STATE ASSESSMENT

The present application is related to U.S. Patent Application PCT/US07/01377, entitled METHOD AND SYSTEM FOR USER SENSITIVE PACING DURING RAPID SERIAL VISUAL PRESENTATION, which is incorporated herein by reference.

BACKGROUND TECHNOLOGY

Rapid serial visual presentation (RSVP) allows high volumes of imagery to be searched efficiently by presenting images at rates of tens or hundreds of milliseconds per image. Hence, RSVP can be used to conduct a triage of high volumes of imagery. A triage generally refers to the rapid identification, sorting, and stratification of images by their likelihood of containing critical information. Images of interest, or targets, can be tagged either through the press of a button, or through neurophysiological signals associated with target detection. For example, it is possible to use an evoked response potential (ERP) in electroencephalogram (EEG) signals as a target detection cue. An ERP is a brief change in the brain's electrical potential in response to critical events in the environment.

The output of the triage process may be a prioritized list of images, with images that elicited a user response being assigned the highest priority, while those images without a user response being assigned a lower priority. Unfortunately, if the output of the triage process is prioritized solely on the basis of ERP, the triage is likely to be inefficient or inadequate. This is because the ERP is only a valid indicator of the presence or absence of a potential target, if images are processed effectively.

While RSVP can be effective when a user is attentive and appropriately fixated on the display screen, a variety of physical and cognitive states can lead to missed targets. The current approaches to RSVP ignore these physical and cognitive states.

In the intelligence community, the ability to extract useful information from the terabytes of intelligence imagery gathered every day is limited by the number of image analysts available and the slow pace of the manual triage process. Surveillance assets routinely capture information that could contribute to tactical successes, and minimize casualties among military personnel and civilians. However, the ability to use this data effectively is contingent on rapid and accurate screening of intelligence imagery. Unfortunately, with the limited number of image analysts available, and the time it takes to process each image, vast numbers of images are not examined properly.

BRIEF DESCRIPTION OF THE DRAWINGS

Features of the present invention will become apparent to those skilled in the art from the following description with reference to the drawings. Understanding that the drawings depict only typical embodiments of the invention and are not therefore to be considered limiting in scope, the invention will be described with additional specificity and detail through the use of the accompanying drawings, in which:

FIGS. 2A and 2B are schematic diagrams depicting triage processes, with a traditional RSVP approach shown in FIG. 2A, and a user sensitive pacing approach shown in FIG. 2B;

FIG. 3 is a chart showing a prioritization and categorization scheme for image triage output.

DETAILED DESCRIPTION

Figure 1:
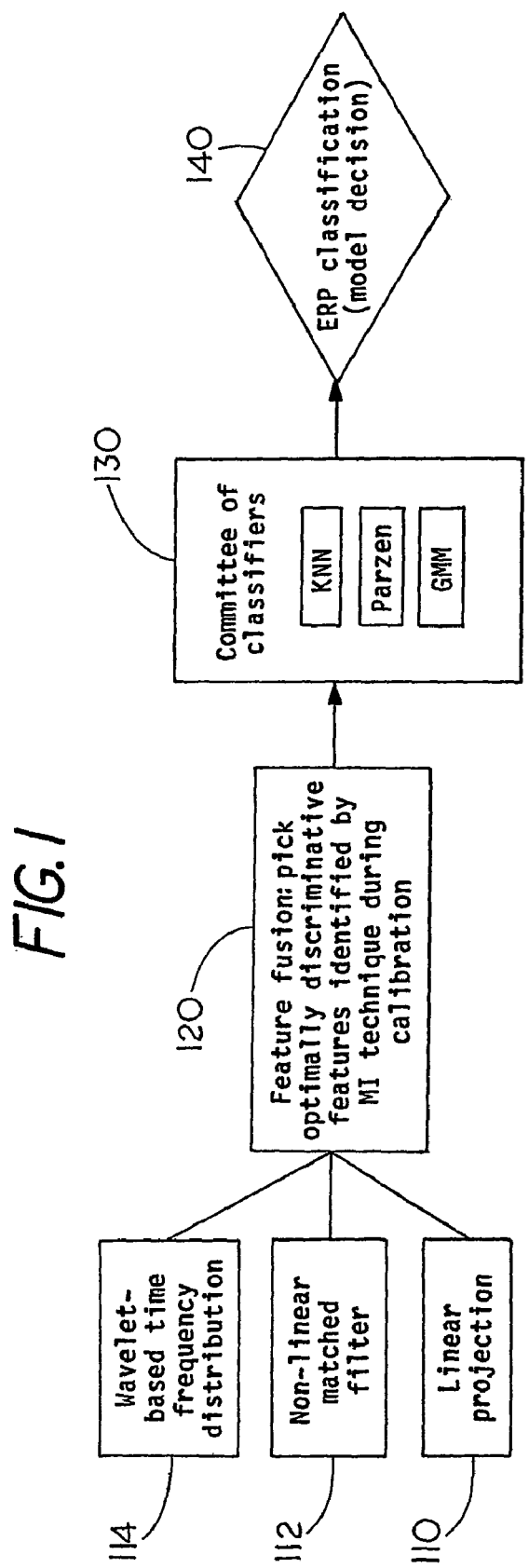
FIG. 1 is a block diagram flowchart showing a fusion detection approach for classification of image data.

In the following detailed description, embodiments are described in sufficient detail to enable those skilled in the art to practice the invention. It is to be understood that other embodiments may be utilized without departing from the scope of the present invention. The following detailed description is, therefore, not to be taken in a limiting sense.

The present invention relates to a method and system that prioritizes the output of an RSVP based image triage system by considering both user responses and estimates of the effectiveness with which each image is likely to have been processed by users. In general, the method for prioritizing an output of an image triage includes monitoring a physical or cognitive state of a user; assigning a first priority to a set of one or more images associated with an optimal user state when a user response is detected; assigning a second priority to a set of one or more images associated with a suboptimal user state when a user response is detected; and assigning a third priority to a set of one or more images associated with an optimal user state when a user response is not detected. A set of one or more images associated with a suboptimal user state can be reexamined when a user response is not detected.

For example, images associated with a user response such as an evoked response potential, processed during optimal user states, are assigned the highest priority for post triage examination as these are highly likely to contain targets. Images without a user response that are processed during optimal user states are assigned the lowest priority, as these are unlikely to contain targets. Images with a user response that are processed during suboptimal states are assigned a medium priority, as these are likely to contain a high number of false positives. Images without a user response, processed during suboptimal user states are flagged for re-processing as these may contain targets that the user may not have detected.

Each image can be tagged with an estimate that can be used, in conjunction with user responses, for post triage image prioritization. The prioritization of triage output by considering the likelihood of false positives and false negatives, which is based on user state assessment, raises the overall efficiency and effectiveness of post triage image analysis.

Estimates of the effectiveness with which a user is likely to have processed images can be derived using a variety of sensors that measure cognitive and physical states associated with visual search. Cognitive states such as attention levels and working memory load are known to affect visual search. Attention levels and working memory load can be estimated using cardiac, EEG, or functional magnetic resonance imaging (fMRI) sensors. Additionally, physical states such as head orientation, eye blinks, eye position, eye scan patterns, and posture have an impact on visual search. These states can be identified using sensors such as head trackers, body worn gyroscopes, eye trackers, and eye electrodes. The image triage system can flag images that were processed improperly due to eye blinks, head movements, drops in attention, or a high working memory load.

The image triage system that utilizes the prioritization technique of the invention can include a variety of RSVP display modalities, so that users have a choice of formats appropriate for their domain. The image triage system can be modular in design, so that other various detection approaches can be easily integrated into the system. The image triage system can support time synchronization and logging for all sensor data and software components. A signal processing module can be used to streamline the flow of data and minimize redundant operations.

By detecting and mitigating suboptimal user states, and thereby raising the effectiveness of the human analyst, the present invention allows intelligence analysts to focus more of their time and effort on analyzing images that are most likely to contain targets. The net result will be more accurate and timely intelligence information for military and political decision makers.

Various aspects of the present invention are described in further detail in the following sections.

Real-Time Detection

The low signal to noise ratio inherent in evoked response potential (ERP) signals presents a difficult challenge for reliable ERP detection. Traditionally, ERP signals are averaged across repeated presentations of stimuli to separate ERP signals from background EEG. Such a solution is impractical in application contexts with real time requirements. The present approach integrates information spatially across electrode sites and examines EEG activity within a short time window around stimulus presentation. This allows the construction of discriminant functions that help distinguish between an ERP signal and background EEG within these temporally restricted windows.

The present detection approach uses a complementary set of fast, single-trial techniques to detect ERP reliably. These include linear projection, a nonlinear matched filter, and estimation of time frequency distributions using wavelets. Each of these approaches contribute to a large pool of features that help discriminate between the presence and absence of ERPs. Classification of ERPs are based on a fusion of these features to a reduced dimensionality representation that maximizes the ratio of relevant discriminative information content to the irrelevant distractive content. A committee of state-of-the-art classifiers with minimal offline training requirements can be employed to obtain the final detection decision.

A. Linear Approach

The linear ERP approach relies on the assumption that measured EEG signals x(t) are a linear combination of distributed source activity s(t) and zero-mean white Gaussian measurement noise n(t), which is defined completely by its second-order statistics: $x(t)=As(t)+n(t)$. Consequently, the optimal ERP detection strategy under this assumption is to determine optimal linear projections of sensor measurement discriminability. For example, in the case of one-dimensional projections, this corresponds to projecting the sensor vector onto a weight vector w, $y(t)=w^T x(t)+b$. The linear projections can be optimized using the traditional Fiser linear discriminant analysis (LDA) criterion, $(m_0-m_1)^2/(\sigma_0^2+\sigma_1^2)$, or alternatively, using the logistic regression technique that assumes the conditional class probability given the projection will follow a logistic model: $P(c|y)=1/(1+e^y)$, which is consistent with the Gaussianity assumption.

While these techniques can provide acceptable levels of performance in some situations, they are restricted in their ability to accommodate any nonlinear amplitude and temporal distortions that the ERP waveforms may exhibit from trial to trial even within the same session with the same subject. Such deviations can render the linearity and Gaussianity assumptions invalid, thus leading to suboptimal detection performance.

B. Nonlinear Matched Filter

The nonlinear matched filter for ERP detection relies on kernel based projection techniques that are used for machine learning. Kernel based transformations provide a way to convert nonlinear solutions into linear solutions via a projection into a higher dimensional space. This approach uses an information theoretic concept called mutual information (MI) to identify optimal parameters for the kernel function used in the projection. The MI is an objective measure of the dependency or nonlinear correlation between two or more random quantities. This suggests that the larger the MI between a set of EEG-based features and the class labels (e.g., background EEG vs. ERP), the better the expected classification accuracy. Hence, the design of a nonlinear projection that maximizes the mutual information between the EEG projection and class labels can be used to create a filter that optimally separates ERP from background EEG activity.

The nonparametric techniques used to design the nonlinear matched filter for ERP detection make minimal assumptions regarding statistics of the underlying data. Additionally, these techniques are mathematically proven to demonstrate very good small-sample size accuracy and fast convergence to the true data statistics as more samples are used by the estimator.

C. Time Frequency Distribution

The ERP waveforms occur at varying times following stimuli presentation, thus it is imperative to take into account the temporal fluctuations in the frequency distribution EEG signals. Since the ERP waveforms are transient in nature, it is important to discover features that capture discriminatory EEG features locally in time. The time frequency distribution (TFD) is constructed using wavelets and can be estimated using Morlet Wavelet decomposition. This decomposition provides an optimal time-frequency resolution for TFD estimation when wavelets are chosen appropriately. The squared-norm of each wavelet filter output provides an estimate of the energy in the time interval and frequency band corresponding to the specific wavelet, and these features are obtained for each EEG site. The spatio-temporal distribution of EEG energy at traditional bands (alpha, beta, theta, etc.) are utilized as the features for discrimination.

While TFDs computed using wavelets provide excellent temporal and frequency resolution, in the interest of computational efficiency and classification accuracy, it is still necessary to separate discriminatory TFD features from non-discriminatory features. To this end, a variant of the best-bases algorithm can be employed. This method expands the EEG signal into orthonormal bases using wavelet packets over a dyadic grid (binary tree). This representation allows for efficient compression of the TFD information, if this tree is pruned using an entropy criterion. The pruning can be based on the MI techniques described earlier. This helps to determine the most efficient and discriminatory sparse signal representation. Once discriminatory features have been identified using MI techniques, the relevant TFD features can be used in conjunction with the linear and nonlinear projection approaches described earlier as the basis for classification.

D. Fusion Detection Approach

While each of the above real-time ERP detection approaches can be used independently of the others in the image triage system, it is also possible to use these approaches jointly in various configurations of two or all three approaches. Such a fusion detection approach for classification is illustrated in the block diagram flowchart of FIG. 1, and relies on extracting the most informative features provided by each ERP detection technique. The three ERP detection approaches described above can be employed to create a pool of potentially useful statistics for ERP detection. As shown in FIG. 1, these include linear projections 110 and nonlinear matched filter projections 112 of raw data, and wavelet-based time frequency distributions 114 of power in EEG signals. This initial pool of features 120 can be diversified to capture a broad range of critical features present in the EEG signals. These features are then evaluated for their optimally discriminatory value using MI based feature ranking algorithms. Feature extraction using MI techniques can be carried out in conjunction with the system calibration process. Once the optimal feature subset is identified, real-time ERP classification will be extremely efficient.

Basing real-time classification on a feature subset that optimizes discriminability among classes allows the ERP decision to be made using classification techniques that require minimal or no online training requirements. Examples of suitable classification techniques include K Nearest Neighbor (KNN), Parzen Windows, and Gaussian Mixture Models (GMM). The KNN and Parzen techniques require no training, while GMM models the underlying data distributions very quickly. These alternative techniques can be used in the context of a committee of classifiers 130, as shown in FIG. 1. The final ERP classification 140 chosen is the modal output decision of the three classifiers.

Each of the ERP detection approaches described above requires similar amounts of training data. The present detection system is calibrated using a set of training images with known truth labels at the beginning of every session. Once calibrated, the ERP detection system provides single trial ERP decisions well within real time constraints.

While the ERP detection system can be initially calibrated in the manner described above, it is also possible to implement an option for the ERP detection system to adapt online during actual use. This is done to compensate for long term EEG non-stationarity. Adaptation can be accomplished by interleaving previously labeled data into the image sequence and tuning the system based on associated EEG responses.

Cognitive State Estimation

The overall classification accuracy of an ERP-based triage system hinges on the effectiveness with which the user will be able to process images. A human analyst, engaged in the process of scanning images, adopts the role of a target sensor. The alert human analyst's target detection abilities far exceed that of any mechanical sensor. However, unlike mechanical sensors that can remain perfectly fixated on the stimuli at every instant, humans exhibit a great deal of variability in their cognitive and physical state over time. Humans blink, get tired, lose attention, and may be drawn to divert their eyes momentarily to other elements in a room. Presenting images at rates of about 20 ms to about 100 ms without any consideration for a user's evolving state is likely to lead to missed targets.

It is important to have ways to determine whether an analyst is likely to have perceived targets and to take steps to mitigate compromised human performance that result in errors. Such errors fall into two broad categories, false positives and false negatives.

False positives occur when the system classifies an image without a target as one with a target. The cost of false positives is largely realized in the form of inefficiency—the incidence of false positives forces analysts to weed out several irrelevant images among images of interest.

False negatives (or misses) occur when images containing a target are incorrectly classified as lacking a target. In many operational contexts, the cost of false negatives may be substantially higher than the cost associated with false positives. If potential targets go undetected in the triage process, vital information may fail to be scrutinized by analysts. The cost of omission may range from the loss of a tactical or strategic advantage, to the loss of lives.

Sub-optimal cognitive and physical states can be detected by various sensors and classifiers that have been adapted to detect sub-optimal user states and invoke mitigation strategies. The sub-optimal states detected and mitigated by the present system are described as follows.

A. User Attention

Maintaining sustained attention over time is a difficult task for most humans. Researchers have noted that subjects performing visual search tasks over long periods of time encounter a vigilance decrement that leads to slower reaction times and increased error rates. However, it has been found that momentary fluctuations in attention levels can be estimated using EEG. For instance, it has been noted that increases in spectral power at 4 Hz and 14 Hz in midline sites accompany periods of low alertness, and that these changes can be used to reliably classify periods of low attention. Cognitive state classifiers can be used in the present system to detect inappropriate levels of attention and adapt the system appropriately to compensate for potential performance decrements.

B. Working Memory

Research suggests that working memory load constrains performance in visual search tasks. Working memory mechanisms play a role in helping individuals distinguish between currently task-relevant and irrelevant stimuli. This is of particular relevance to the task domain of the intelligence image analyst where users will be dealing with varied and ambiguous targets and distractors. Reducing availability of working memory in the context of sustained attention tasks can compromise performance on target detection tasks.

The present approach incorporates EEG-based classifiers to assess a user's working memory load. Research indicates that increases in working memory demands contribute to an increase in frontal midline theta and a decrease in parietal alpha. Classifiers are employed to assess a user's evolving cognitive load. As working memory loads approach levels that could negatively affect performance, the system can adapt to mitigate the risk associated with suboptimal performance.

C. Gross Eye Activity

At the 20 ms to 100 ms rate of presentation common in RSVP tasks, a variety of normal eye activities can prevent images from being analyzed. Eye blinks occur at an average frequency of one every six seconds and last for an average duration of 80 to 100 milliseconds. Images presented in conjunction with eye blinks are unlikely to be processed very effectively. Over the span of sessions lasting tens of minutes, eye blinks could result in hundreds of images going by without an appropriate degree of visual processing by the analyst. Unfortunately, eye blinks are only one example of eye activity that can impact performance. Large eye saccades, such as a momentary glance away from the screen to relieve eye strain or to attend to an external event could cause images to go by without being assessed by the analyst.

Fortunately, many of these eye events can be detected using EEG eye electrodes and unobtrusive desktop eye trackers. Specific ways in which the present system can use information from these sensors to mitigate the detrimental impact of common activity will be discussed hereafter.

D. Head Orientation

Like the information provided by sensors assessing eye activity, assessments of head orientation provide a way to determine whether the subject is likely to perceive information presented on the screen. It is natural for users to vary the orientation of their head over the course of a sustained period of time. Users may have to refer to other sources of information, monitor events in the surrounding environment, and vary position to relieve fatigue. In the context of a user reviewing images in RSVP contexts, these routine actions could lead to missed images. Many of these actions occur frequently and may not even be something users are consciously aware of as they work on tasks. Hence, users may not think to pause the presentation. Small unobtrusive head trackers can be employed to detect head positions that could compromise performance. Specific ways in which the present system can use information from these sensors to mitigate the detrimental impact of common activity will be discussed hereafter.

Human Performance Optimization

The image triage system described herein leverages the unsurpassed strengths of the human analyst in target detection tasks, while minimizing human limitations. While it may be tempting to think of the analyst as being capable of fixating and attending to images at high rates, over sustained periods of time, the human is a complex system whose performance waxes and wanes. The present system allows users to process images at their maximum possible capacity, whatever that might be, at any instant. Towards this end, three mitigation techniques can be employed in the system: user alerts, user sensitive pacing, and user sensitive prioritization, which are described as follows.

A. User Alerts

One technique that the triage system can employ to engage the user optimally is to alert the user when certain suboptimal states are detected. Aural and visual cues serve to notify users that they may not be processing images effectively. Such aural and visual alerts are reserved for sustained lapses only. That is, for lapses that extend for tens of seconds or minutes.

B. User Sensitive Pacing

Many of the cognitive and physical states that can compromise performance are frequent and brief. Eye blinks, gross eye movements, and momentary lapses in attention are likely to occur frequently and be beyond the control or conscious awareness of the user. Reminders in response to these frequent events could be frustrating and distracting to the user. A technique called user sensitive pacing is used to mitigate these events.

The user sensitive pacing technique optimizes the flow of images to the analyst in real time. This allows for images to be presented at a pace that is as high as an analyst can effectively handle at any instant. This is done by using the cognitive and physical state sensing techniques described earlier. FIGS. 2A and 2B are schematic diagrams depicting triage processes, with a traditional RSVP approach 210 shown in FIG. 2A, and a user sensitive pacing approach 250 shown in FIG. 2B.

FIG. 2A shows the consequences of suboptimal states on triage effectiveness for the traditional RSVP approach 210. During analysis of a set of images 212, an eye blink 214 or a fall in attention 216 results in one or more missed images 220, which are never further considered. This results in a less than effective triage process, which can result in detrimental consequences such as false negatives and false positives.

In the user sensitive pacing approach 250 shown in FIG. 2B, the physical and cognitive states described previously are taken into consideration for distinct pacing interventions. For instance, during analysis of a set of images 252, user sensitive pacing accommodates for eye blink 254. Once a blink is detected, the image index is set to the image immediately preceding the blink. The missed image sequences 260 are cached in memory so that fast re-indexing can occur without perceivable interruption to the user. The image frames affected by the eye blinks can then be re-visited when desired. Additionally, gross eye saccades that lead to fixation away from the image screen will cause the presentation of images to pause. The current image index is then moved to the image that occurred just prior to the beginning of the saccade. The presentation of images will resume as soon as the eyes return to appropriate fixation regions. Head movements can be treated in a way similar to eye saccades.

In the user sensitive pacing approach, attention and working memory assessments serve to control the rate of image presentation. As shown in FIG. 2B, if there is a fall in attention 270, then an image presentation rate 272 is adjusted appropriately. Thus, as a user's attention level wanes or working memory load begins to increase, the pace of image presentation can be reduced. For example, at low working memory load and high attention levels, images can be presented at rates of about 20-100 ms. At medium levels of attention and working memory, the presentation rate can be reduced to an image at about every 200 ms. At a high working memory and low attention levels, image presentation may be temporarily reduced to one at about every 300 ms. These presentation rates are for illustration only as other rates might be more appropriate in a particular analysis context.

Image sensitive pacing allows users to interact in a natural manner with the triage system. Users will not have to deal with unreasonable demands on their physical or cognitive state. Instead, the system continually adapts to the user. User sensitive pacing allows the system to leverage user strengths while minimizing the impact of normal human vulnerabilities in RSVP tasks.

The user sensitive pacing technique is described further in copending U.S. Patent Application PCT/US07/01377, entitled METHOD AND SYSTEM FOR USER SENSITIVE PACING DURING RAPID SERIAL VISUAL PRESENTATION, which is incorporated herein by reference.

C. User Sensitive Prioritization

While user sensitive pacing is used to maximize the likelihood that images are processed appropriately during analysis, user sensitive prioritization is used to organize the output of the triage process after analysis. User sensitive prioritization relies on ERP-based target classification, in combination with assessments of cognitive and physical state, to categorize and prioritize scanned images. Image categorization is done in terms of the likelihood of containing targets.

For example, images that elicit an ERP and occur during nominal (optimal) user states are classified as likely true positives. Images that do not elicit an ERP and occur during nominal user states are classified as likely true negatives. Images that elicit an ERP and occur during sub-optimal user states are classified as potential false positives. Images that do not elicit an ERP and occur during sub-optimal user states are classified as potential false negatives.

Once the outputs of the ERP based triage are categorized, the outputs can be prioritized for closer review by the analyst. FIG. 3 is a chart showing the categorization and prioritization of triage output, and summarizes one possible prioritization scheme that can be used by the present triage system. The ideal prioritization scheme will vary by context and can be specified by the user.

As indicated by FIG. 3, images that are viewed during periods of optimal user state, and elicit an ERP, are assigned the highest priority for post triage review as targets are likely. Images that elicit an ERP, but occur during suboptimal user states, are assigned a lower (medium) priority as targets are less likely. Images that do not produce an ERP, but occur during optimal user states are assigned the lowest priority, as the likelihood of targets being present in these images will be quite low. Images that do not produce an ERP and occur during suboptimal user states are labeled for rescanning as the target status is unknown.

User sensitive prioritization provides a way to distinguish between true negatives and false negatives. Without independent assessment of user state as described herein, such disambiguation becomes impossible.

Image Triage System

Figure 4:
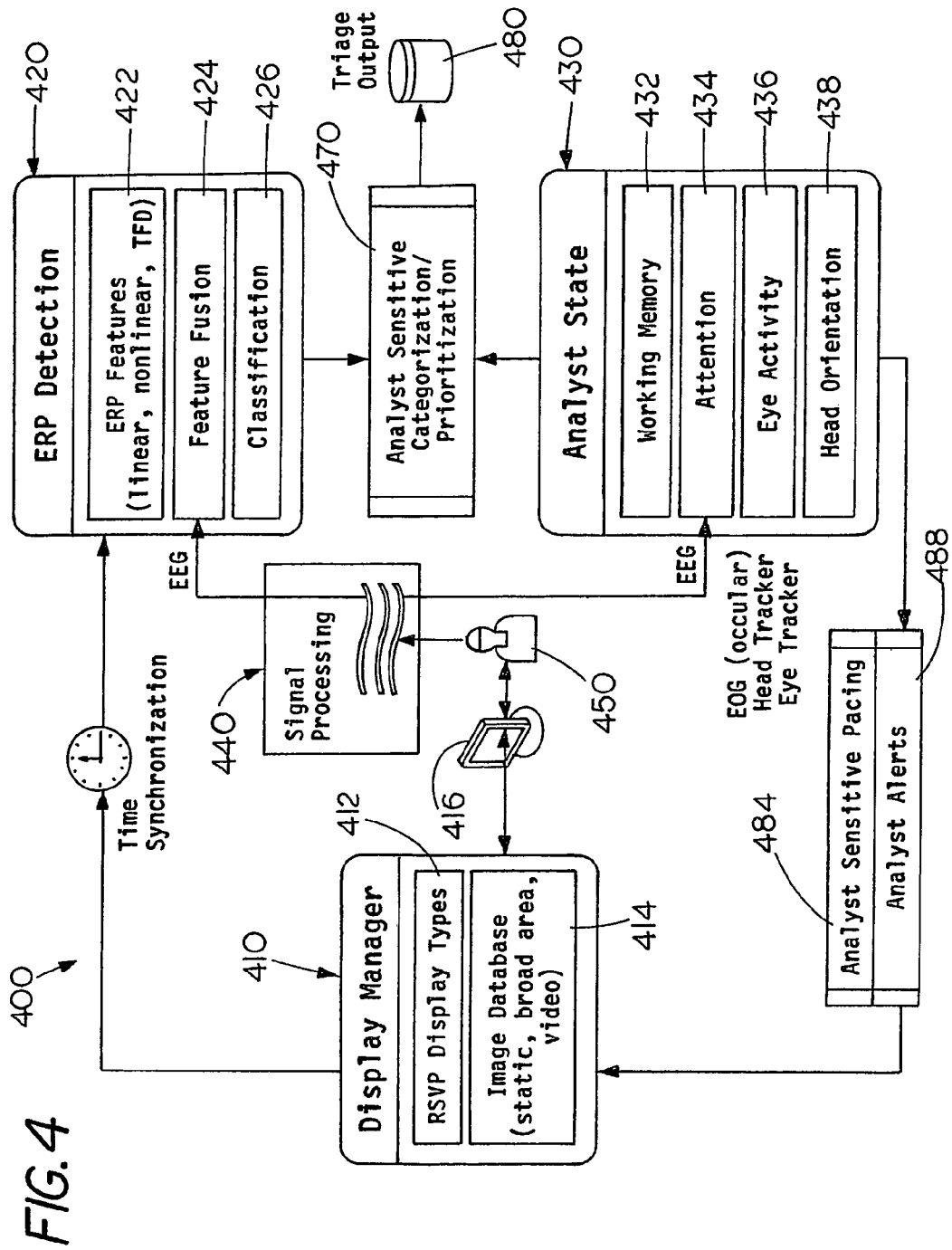
FIG. 4 is a schematic depiction of one embodiment of an image triage system.

FIG. 4 is a schematic depiction of one embodiment of an image triage system 400 according to the present invention, which has modular system components. Various software and hardware components are used to provide a real-time triage system. The modular architecture design allows easy integration of new software or hardware components if desired. The triage system 400 streamlines the handling of data, eliminates redundant processing, supports logging, provides precise time synchronization, and supports RSVP display formats relevant to various types of imagery. As shown in FIG. 4, the image triage system 400 generally includes a display module 410, a detection module 420, and a sensor module 430, all of which are in operative communication with each other. A base station computer can be used to control the triage system and can communicate with the system via a wireless network or Ethernet connection.

The display module 410 provides a means for managing images that are shown to a user. The image triage system 400 integrates an RSVP interface display 412 and an image database 414, which are part of display module 410. The interface display 412 can use a variety of different RSVP presentation formats that are shown on a display screen 416 to a user. Given the fact that analysts deal with information from a broad range of information sources, the present system provides the analyst a choice of interfaces. Examples of interface display modalities that can be provided by the system are keyhole, carousel, and floating displays.

Keyhole RSVP displays present images in a slideshow format, with all images being displayed at the same location. This modality may be most suited for static imagery. Carousel RSVP displays present several images on the screen at the same time. Images start from the left, displayed in a small format, and grow in size until they reach the top of the screen, and diminish in size as they move to the right. A variant of the carousel display may be appropriate for processing broad area imagery as it provides a sense for surrounding spatial context. Floating RSVP displays extend a series of frames into a 3-D trail. The frame in the foreground is analogous to a vehicle windshield. Frames in the distance begin approaching the user and fade away. Floating RSVP is particularly effective for detecting targets within video frames.

Display modalities like carousel and floating RSVP provide users with a broader sense for spatiotemporal dynamics of a scene than the keyhole display. In many application domains, the broader context provided by these schemes may improve target detection relative to the narrow perspective provided by the keyhole display.

The image database 414 can include a variety of different image types such as static and broad area images, video clips, image chips, and the like. Image chips are produced from a large image that is "cut up" into a series of smaller images that are presented one after the other.

The detection module 420 provides a means for detecting ERP in a user. The detection module 420 employs an integrated real-time ERP feature detection system 422 that can include one or more of the various components discussed previously, such as linear projection, nonlinear matched filters, and estimations of time frequency distributions using wavelets. A feature fusion system 424 can also be implemented to provide for complementary use of these techniques such as in the fusion approach described above with respect to FIG. 1. This adds redundancy and robustness to the triage system and improves overall ERP detection accuracy. A cognitive classification system 426 is also part of detection module 420.

The sensor module 430 provides a means for monitoring the physical and cognitive state of an analyst user. The sensor module 430 can include various standard sensor components used to detect the state of the analyst user. Such sensor components can include sensors for monitoring working memory 432, user attention 434, eye activity 436, and head orientation 438.

For example, EEG data can be collected using the BioSemi Active Two system. This system has a 32 channel EEG cap and a set of eye electrodes. The eye electrodes provide information concerning eye blinks and eye saccades. The BioSemi system integrates an amplifier with an Ag—AgCl electrode, which affords extremely low noise measurements without any skin preparation. Information about head orientation can be provided by, for example, the InertiaCube. The InertiaCube provides orientation information about the head's pitch, roll, and yaw axes. Information from these sensors can be processed on a standard personal computer (PC). User gaze can be tracked with an unobtrusive desk mounted tracking system that provides face, eye, eyelid and gaze tracking using a completely non-contact, video-based sensor. The sensors can be connected to the PC via a combination of USB ports, serial ports, or Bluetooth wireless interfaces.

A signal processing module 440 provides a means for processing signals from the sensor module 430 prior to feature extraction and classification by detection module 420. The signal processing module 440 can incorporate one or more signal drift correction filters or bandpass filters. For example, filters can be used that correct for DC drift of signals over time. Bandpass filters can be implemented to allow signal processing components to extract frequency bands of interest for further analysis.

The signal processing module 440 can incorporate components to correct for eye blink artifacts. Effective decontamination of eye activity is particularly important for ERP classification. High amplitude noise associated with eye activity contributes to the overall challenge of reliably detecting ERPs. An adaptive linear ocular filter that removes eye blink artifacts from EEG signals can be used and is available from Honeywell.

The signal processing module 440 can also incorporate components to provide power spectral density (PSD) estimates. Classifiers associated with attention and cognitive load, use estimates of spectral power at various frequency bands as input features for classification. To minimize redundant operations, a single component can be used to generate PSD estimates and propagate them to components that rely on PSD estimates as input features. The PSD of EEG signals can be estimated using the Welch method. The PSD process uses 1-second sliding windows with 50% overlap. PSD estimates are integrated over five frequency bands: 4-8 Hz (theta), 8-12 Hz (alpha), 12-16 Hz (low beta), 16-30 Hz (high beta), and 30-44 Hz (gamma). These bands sampled every 0.1 seconds can be used as the basic input features for cognitive classification. The particular selection of the frequency bands is based on well-established interpretations of EEG signals in prior cognitive and clinical contexts.

During operation of image triage system 400, a user 450 looks at display screen 416 that is provided with a set of images for analysis from image database 414 of display module 410. The sensors worn by the user as part of sensor module 430 detect signals generated from the physical and cognitive state of the user. These signals are processed by signal processing module 440 for use by detection module 420 in detecting the ERP in user 450. The images viewed by user 450 are time synchronized so that they correspond with the detected ERP.

The detection module 420 and sensor module 430 communicate with an analyst sensitive categorization/prioritization system 470 as shown in FIG. 4, which provides a means for assigning a various priorities to sets of one or more images associated with optimal or suboptimal user states when a user response is detected or not detected. The analyst sensitive prioritization system 470 can be implemented using various computer hardware and software components. The triage output can be sent to a storage device 480 for post triage examination of images. The storage device 480 also provides a means for reexamining images associated with a suboptimal user state when a user response is not detected.

In the analyst sensitive prioritization system 470, images associated with a user response, processed during optimal user states, are assigned the highest priority for post triage examination. Images without a user response that are processed during optimal user states are assigned the lowest priority. Images with a user response that are processed during suboptimal states are assigned a medium priority. Images without a user response, processed during suboptimal user states are flagged for re-processing.

Although not required, the image triage system 400 can also implement an analyst sensitive pacing system 484 and/or an analyst alert system 488, which are in communication with sensor module 430 and display module 410 as depicted in FIG. 4.

Instructions for carrying out the various methods, process tasks, calculations, control functions, and the generation of signals and other data used in the operation of the system are implemented, in some embodiments, in software programs, firmware or computer readable instructions. These instructions are typically stored on any appropriate medium used for storage of computer readable instructions such as floppy disks, conventional hard disks, CD-ROM, flash memory ROM, nonvolatile ROM, RAM, and other like medium.

The present invention may be embodied in other specific forms without departing from its essential characteristics. The described embodiments are to be considered in all respects only as illustrative and not restrictive. The scope of the invention is therefore indicated by the appended claims rather than by the foregoing description. All changes that come within the meaning and range of equivalency of the claims are to be embraced within their scope.

What is claimed is:

1. A method for prioritizing an output of an image triage, comprising:
   displaying images to a user on a display screen;
   using one or more sensors to monitor a physical state or cognitive state of the user while displaying the images to the user;
   detecting an evoked response potential (ERP) in the user while displaying the images to the user;
   classifying the user as being in one of two distinct user states based on the monitored physical state or cognitive state of the user, the two distinct user states being an optimal user state or a suboptimal user state; and
   in a user sensitive prioritization system:
      assigning a first priority to a set of one or more of the images when the user is classified as being in the optimal user state and an ERP is detected;
      assigning a second priority to a set of one or more of the images when the user is classified as being in the suboptimal user state and an ERP is detected; and
      assigning a third priority to a set of one or more of the images when the user is classified as being in the optimal user state and an ERP is not detected.

2. The method of claim 1, further comprising reexamining a set of one or more of the images when the user is classified as being in the suboptimal user state and an ERP is detected.

3. The method of claim 1, wherein the image triage comprises a rapid serial visual presentation.

4. The method of claim 1, wherein the physical state or cognitive state of the user is monitored by one or more sensors.

5. The method of claim 4, wherein the physical state of the user comprises one or more of head orientation, eye blinks, eye position, eye scan patterns, or body posture.

6. The method of claim 4, wherein the cognitive state of the user comprises one or more of attention level or working memory load.

7. The method of claim 1, wherein the first priority is higher than the second priority, and the second priority is higher than the third priority.

8. The method of claim 1, wherein the user response is an evoked response potential.

9. The method of claim 8, wherein the evoked response potential is detected by one or more techniques comprising a linear projection, a nonlinear matched filter, or a wavelet-based time frequency distribution.

10. An image triage system, comprising:
    a display module configured to display a plurality of images to a user;
    a detection module in operative communication with the display module and configured to detect an evoked response potential (ERP) in the user;
    a sensor module in operative communication with the display module and the detection module and configured to sense a physical state or cognitive state of the user while displaying the images to the user and, based on the sensed physical state or cognitive state, classify the user as being in one of two distinct user states, the two distinct user states being an optimal user state or a suboptimal user state;
    a signal processing module in operative communication with the sensor module and the detection module and configured to process signals therefrom; and
    a user sensitive prioritization system in operative communication with the detection module and the sensor module;
    wherein the user sensitive prioritization system assigns various priorities to sets of one or more of the plurality of images based upon (i) whether the user is classified as being in the optimal or suboptimal user state and (ii) whether an ERP is detected or not detected.

11. The system of claim 10, wherein the display module comprises a rapid serial visual presentation display, and an image database.

12. The system of claim 10, wherein the evoked response potential feature detection system comprises a linear projection, a nonlinear matched filter, a wavelet-based time frequency distribution, or combinations thereof.

13. The system of claim 10, wherein the detection module comprises a feature fusion system.

14. The system of claim 10, wherein the detection module comprises a cognitive classification system.

15. The system of claim 10, wherein the sensor module comprises one or more of a working memory sensor, a user attention sensor, an eye activity sensor, or a head orientation sensor.

16. The system of claim 10, wherein the signal processing module comprises one or more signal drift correction filters, bandpass filters, linear ocular filters, or components to provide power spectral density estimates.

17. The system of claim 10, further comprising an output storage device for post triage examination of the plurality of images.

18. The system of claim 10, further comprising one or more of a user sensitive pacing system or a user alert system, which are in communication with the sensor module and the display module.

* * * * *